US00PP20317P3

(12) United States Plant Patent
Sheehan

(10) Patent No.: US PP20,317 P3
(45) Date of Patent: Sep. 15, 2009

(54) GRAPEVINE 'SHEEGENE-14'

(50) Latin Name: *Vitis vinifera*
Varietal Denomination: Sheegene-14

(76) Inventor: Timothy P. Sheehan, 120 Olivewood Ct., Porterveille, CA (US) 93257

( * ) Notice: Subject to any disclaimer, the term of this patent is extended or adjusted under 35 U.S.C. 154(b) by 50 days.

(21) Appl. No.: 11/897,630

(22) Filed: Aug. 30, 2007

(65) Prior Publication Data

US 2009/0064382 P1 Mar. 5, 2009

(51) Int. Cl.
*A01H 5/00* (2006.01)

(52) U.S. Cl. ..... Plt./207

(58) Field of Classification Search ..... Plt./207
See application file for complete search history.

*Primary Examiner*—June Hwu
(74) *Attorney, Agent, or Firm*—Baker Manock & Jensen, PC; Eric C. Cole

(57) ABSTRACT

A new and distinct variety characterized by a green-colored, large sized seedless grape that ripens during the first week of September, approximately four weeks later than the Thompson Seedless Grape (unpatented) when grown in the San Joaquin Valley of Central California. The grapes of this new variety are produced on strong woody branches and are well adapted to commercial handling.

1 Drawing Sheet

Latin name of the genus and species of the plant claimed: The claimed plant relates to a new and distinct variety of *Vitis vinifera* to be known as 'Sheegene-14'.

Variety denomination: This invention relates to a new discovery and asexual reproduction of a new variety of *Vitis vinifera*. The new variety was first hybridized by Timothy P. Sheehan of Porterville, Calif. in Spring 2000; first flowering occurred in May 2003. The pollen parent is Autumn Seedless (unpatented) and the seed parent is Red Globe (U.S. Plant Pat. No. 4,787). The new variety was asexually propagated in the dormant season of 2003/2004, bud grafted on Harmony, virus-free rootstock, in a *Vitis vinifera* variety block located near Fowler, Calif. on the west side of Thompson Road, north of Adams Road. The green-colored seedless grapes produced by the new variety are large in size and mature approximately four weeks later than Thompson Seedless (unpatented). The new variety has been shown to maintain its distinguishing characteristics through asexual propagation.

The new variety is distinguished from its pollen parent, Autumn Seedless (unpatented), as compared in that the new variety produces green-colored seedless grapes to the white-colored grapes produced by the pollen parent, Autumn Seedless (unpatented). The new variety is distinguished from its seed parent, Red Globe (U.S. Plant Pat. No. 4,787), in that the new variety produces green-colored seedless grapes, as compared to its seed parent, Red Globe (U.S. Plant Pat. No. 4,787), that produces red-colored seeded grapes.

BACKGROUND OF THE INVENTION

The present invention relates to a new and distinct variety of grape which will hereinafter be denominated as 'Sheegene-14' and more particularly as a grapevine which produces a large, green-colored seedless grape that matures approximately during the first week of September in the San Joaquin Valley of Central California. The new invention most closely resembles Thompson Seedless (unpatented) but it produces a larger grape that is very sweet, has very good flavor, and matures approximately four weeks later.

SUMMARY OF THE INVENTION

The 'Sheegene-14' grapevine is characterized by producing a large size green seedless grape with very good flavor that is mature for harvesting and shipment in approximately the first week of September in the San Joaquin Valley of Central California. The new variety can be compared to Thompson Seedless (unpatented) but the grapes mature approximately four weeks later, among other distinguishing characteristics.

BRIEF DESCRIPTION OF THE DRAWINGS

The accompanying drawing is a colored photograph of the grapes produced by the subject variety; several leaves are displayed as well as a typical section of the vine. Across the top of the color photograph to the left and center are secondary growth clusters; to the right is a mature leaf displaying the upper surface and petiole. Across the middle of the color photograph on the left is a mature grape cluster; in the center on the top is a shoot and tendrils and small leaves; in the center on the bottom are five berries (three longitudinally and two horizontally) displaying the flesh and shape; to the right is a shoot and tendrils and small leaves. Across the bottom of the color photograph to the left a mature leaf displaying the bottom surface; and to the right is a mature cane displaying tendrils, nodes, and small leaves.

DETAILED BOTANICAL DESCRIPTION

Referring more to the horticultural description of the new and distinct variety of grapevine, the following has been observed under the ecological conditions prevailing at the origin vineyard that is located east of Fowler, Calif. in the San Joaquin Valley of Central California.

All major color descriptions are by reference to the Dictionary of Color by Maerz and Paul, First Edition, published in 1930. Common color names are also used in several instances.

VINE

Size: 5 feet (1.52 meters) in height, 30 to 36 inches (76.20 to 91.44 cm) in width.
Vigor: Very good.
Figure (form): With wide cordons forming a "T" shape.
Production: Very good.
Regularity of bearing: Regular.

TRUNK

Size: Medium; 6 inches (15.24 cm) in circumference, 28 inches (71.12 cm) above graft.
Surface texture: Rough, shaggy.
Color: Pl.7 E10 Chestnut Brown Stone.
Mature cane color: Pl.14 L12 Sudan Brown.
Nodes: Five on canes, 23⅓ inches (59.27 cm) long.
Length between nodes: 5 inches (12.7 cm).
Lenticel number: 0.
Lenticel size: 0.
Shoot size: Medium.
Shoot length: 2.24 inches (56.9 mm).
Shoot shape: Droopy.
Tendril number: 1.
Tendril size: 2.24 inches (56.9 mm).
Tendril location: At nodes.
Tendril form: Bifurcate.
Tendril texture: Firm.
Bud shape: Convex.
Bud size: 0.24 inches (6 mm) in length; 0.31 inches (8 mm) in width.
Bud fruitfulness: Very good.
Bud break date: N/A.

BRANCHES

Size: Medium; 2 inches (5.08 cm) in circumference.
Cordons: 36 inches (91.44 cm) on one side of vine trunk; 30 inches (76.20 cm) on other side of vine trunk.
Color (one year or older wood): Pl.7 H9 Liver Brown+, Autumn Oak−.
Color (immature branches): Pl.19 L6 Calliste Green.

LEAVES

Size: Large.
Density: Dense.
Average length: 6½ inches (16.51 cm).
Average width: 9¼ inches (23.5 cm).
Form: Pentagonal.
Texture (upper surface): Smooth.
Texture (lower surface): Glabrous.
Color (upwardly disposed surface): Pl.23 J8 Mt. Vernon Green.
Color (downwardly disposed surface): Pl.20 K6 Piquant Green.
Color (leaf vein): Pl.19 L5 Cosse Green.
Petiole size: Large.
Petiole color: Pl.19 L5 Cosse Green.
Petiole length: 6⅜ inches (16.5 cm).
Petiole thickness: 0.20 inches (5 mm).
Petiole sinus form: Upside down "U" shape.
Lobes: Four.
Tooth size: 0.47 to 0.51 inches (12 to 13 mm) in width.
Tooth number: Three to four.
Tooth shape: Convex (triangular).

INFLORESCENCE

Size: 8 to 9 inches (20.32 to 22.86 cm).
Number borne per spur: Two.
Number borne per vine: 20 to 25.

FLOWERS

Flower buds (size): Small.
Flower buds (surface): Glabrous.
Flower buds (quantity): Moderate.
Date of bloom: Apr. 26, 2007.
Date of full bloom: May 4, 2007.
Size of bloom: 0.078 inches (2 mm).
Petal color: Pl.21 E4 Fern.
Petal size: 0.078 to 0.12 inches (2 to 3 mm).
Pistil color: Pl.17 L7 Viridine y.
Amount of pollen: No Data Available.
Date of first visible berries: May 4, 2007.

FRUIT

Solids: 21.6° Brix.
Acid: 0.55.
Sugar/acid ratio: 39.2.
Juice pH: 3.81.
Seeds: None.
Capstem pedicel: 0.24 inches (6 mm).
Berry weight: Approximately 11.36 grams.
Juice color: Pl.17 A6 Opaline Green.
Size: Large.
Cluster size: Large.
Cluster (average length not including main stem): 11 inches (27.94 cm).
Cluster (average diameter at greatest width): 9½ inches (24.13 cm).
Cluster weight: 1704 grams (3¾ lbs.).
Compact: Compact.
Cluster form: Conical.
Stems: Medium; 3.23 inches (8.2 cm).
Stem caliper: 0.20 inches (0.5 mm).
Berry size: Large.
Berry form: Ovate.
Berry number: Approximately 88.
Berry size (average dimension in longitudinal axis): 1.01 inches (25.6 mm).
Berry size (average dimension in transverse axis): 0.87 inches (22 mm).

SKIN

Thickness: Thin.
Texture: Tough.
Tendency to crack: Unknown.
Blush color: Pl.19L6 Calliste 9.
Ground color: None.
Pulp: Clear.
Lenticels: Yes.

FLESH

Flesh color: Pl. 17L7 Vividine Wine.
Juice production: Very good.
Flavor: Very good.
Aroma: Very mild.
Texture: Firm.

Ripening: Even.
Eating quality: Very good.
Use: Fresh market.
Keeping quality: Very good.
Resistance to disease: None observed.
Harvesting: Late August to September in the San Joaquin Valley of Central California.
Shipping and handling qualities: Good.
U.S.D.A hardiness zone: Zones 8 and 9.

Having thus described and illustrated our new variety of grapevine, we claim:

1. A new variety of grapevine to be known as 'Sheegene-14', substantially as illustrated and described, characterized principally by its production of green-colored, large sized seedless grapes, that mature approximately four weeks later in the season of ripening than does the Thompson Seedless Grape (unpatented) that it closely resembles.

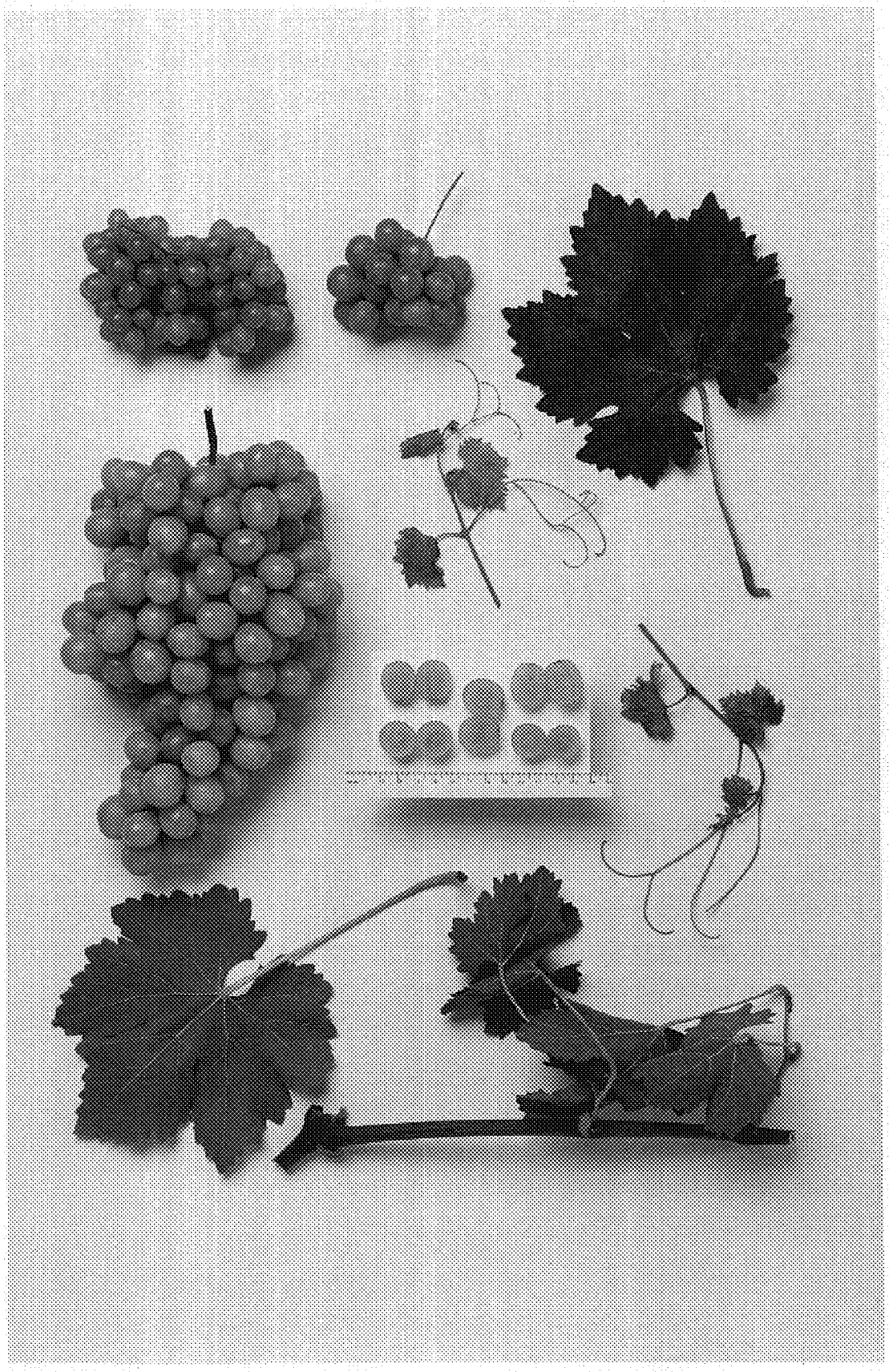

* * * * *